(12) United States Patent
Schmiel et al.

(10) Patent No.: US 7,597,695 B2
(45) Date of Patent: *Oct. 6, 2009

(54) POSTERIOR OBLIQUE LUMBAR ARTHRODESIS

(75) Inventors: Daniel G. Schmiel, Edina, MN (US); Rodney L. Houfburg, Prior Lake, MN (US); Daniel D. McPhillips, Ham Lake, MN (US); William C. Welch, Sewickley Heights, PA (US)

(73) Assignees: Zimmer Spine, Inc., Minneapolis, MN (US); University of Pittsburgh of the Commonwealth System of Higher Education, Pittsburgh, PA (US)

( * ) Notice: Subject to any disclaimer, the term of this patent is extended or adjusted under 35 U.S.C. 154(b) by 324 days.

This patent is subject to a terminal disclaimer.

(21) Appl. No.: 11/364,413

(22) Filed: Feb. 27, 2006

(65) Prior Publication Data
US 2006/0200238 A1   Sep. 7, 2006

Related U.S. Application Data

(60) Division of application No. 09/921,008, filed on Aug. 2, 2001, now Pat. No. 7,033,392, which is a continuation-in-part of application No. 09/630,793, filed on Aug. 2, 2000, now Pat. No. 6,626,905.

(51) Int. Cl.
*A61B 17/56* (2006.01)
(52) U.S. Cl. .......................... 606/90; 606/279; 600/235
(58) Field of Classification Search .................. 606/60, 606/61, 90, 246, 248, 249, 279; 623/17.11, 623/17.12, 17.13, 17.14, 17.15, 17.16; 600/235
See application file for complete search history.

(56) References Cited

U.S. PATENT DOCUMENTS

| | | | |
|---|---|---|---|
| 3,848,601 | A | 11/1974 | Ma et al. |
| 4,501,269 | A | 2/1985 | Bagby |
| 4,653,481 | A | 3/1987 | Howland et al. |
| 4,743,256 | A | 5/1988 | Brantigan |
| 4,805,602 | A | 2/1989 | Puno et al. |
| 4,834,757 | A | 5/1989 | Brantigan |
| 4,877,020 | A | 10/1989 | Vich |

(Continued)

FOREIGN PATENT DOCUMENTS

EP           0307241        3/1989

(Continued)

OTHER PUBLICATIONS

SulzerMedica Sulzer Spine-Tech, *Posterior 4022 Paddle Tube Surgical Technique, BAK™ Lumbar Interbody Fusion System*, Brochure, 25 pgs., 1998.

(Continued)

*Primary Examiner*—Ralph A Lewis
(74) *Attorney, Agent, or Firm*—Crompton, Seager & Tufte, LLC.

(57) ABSTRACT

Instruments and methods for spinal stabilization are disclosed. In preferred embodiments, the invention provides greater stabilization of vertebral bodies through methods including combinations of external fixation systems and intervertebral implants to provide greater fusion stability, greater motion segment stability, faster fusion, reduced pain, reduced chance of migration, reduced chance of subsidence, etc.

14 Claims, 8 Drawing Sheets

U.S. PATENT DOCUMENTS

| | | |
|---|---|---|
| 4,961,740 A | 10/1990 | Ray et al. |
| 5,000,165 A | 3/1991 | Watanabe |
| 5,015,247 A | 5/1991 | Michelson |
| 5,015,255 A | 5/1991 | Kuslich |
| 5,026,373 A | 6/1991 | Ray et al. |
| 5,055,104 A | 10/1991 | Ray |
| 5,306,275 A | 4/1994 | Bryan |
| 5,357,983 A | 10/1994 | Mathews |
| 5,458,638 A | 10/1995 | Kuslich et al. |
| 5,484,437 A | 1/1996 | Michelson |
| 5,484,638 A | 1/1996 | Crabtree |
| 5,489,307 A | 2/1996 | Kuslich et al. |
| 5,489,308 A | 2/1996 | Kuslich et al. |
| 5,505,732 A | 4/1996 | Michelson |
| 5,534,031 A | 7/1996 | Matsuzaki et al. |
| 5,549,608 A | 8/1996 | Errico et al. |
| 5,554,157 A | 9/1996 | Errico et al. |
| 5,584,831 A | 12/1996 | McKay |
| 5,586,984 A | 12/1996 | Errico et al. |
| 5,609,636 A | 3/1997 | Kohrs et al. |
| 5,645,598 A | 7/1997 | Brosnahan, III |
| 5,658,337 A | 8/1997 | Kohrs et al. |
| 5,722,977 A | 3/1998 | Wilhelmy |
| 5,741,253 A | 4/1998 | Michelson |
| 5,749,916 A | 5/1998 | Richelsoph |
| 5,772,661 A | 6/1998 | Michelson |
| 5,776,196 A | 7/1998 | Matsuzaki et al. |
| 5,797,909 A | 8/1998 | Michelson |
| 5,800,550 A | 9/1998 | Sertich |
| 5,803,904 A | 9/1998 | Mehdizadeh |
| 5,860,973 A | 1/1999 | Michelson |
| 5,863,293 A | 1/1999 | Richelsoph |
| 5,865,847 A | 2/1999 | Kohrs et al. |
| 5,928,242 A | 7/1999 | Kuslich et al. |
| 5,947,971 A | 9/1999 | Kuslich et al. |
| 5,964,760 A | 10/1999 | Richelsoph |
| 5,984,922 A | 11/1999 | McKay |
| 6,010,503 A | 1/2000 | Richelsoph et al. |
| 6,030,390 A | 2/2000 | Mehdizadeh |
| 6,520,967 B1 | 2/2003 | Cauthen |
| 6,626,905 B1 | 9/2003 | Schmiel et al. |
| 7,033,392 B2 * | 4/2006 | Schmiel et al. .......... 623/17.11 |

FOREIGN PATENT DOCUMENTS

| | | |
|---|---|---|
| WO | WO9848738 | 11/1998 |
| WO | WO9959481 | 11/1999 |
| WO | WO0128437 | 4/2001 |
| WO | WO0162166 | 8/2001 |

OTHER PUBLICATIONS

Zhao, J. et al., Spine, *Posterior Lumbar Interbody Fusion Using Posterolateral Placement of a Single Cylindrical Threaded Cage*, vol. 25, No. 4, pp. 425-430, Feb. 2000.

SulzerMedica Sulzer Spine-Tech, *Posterior 4022 Tooth Tube Surgical Technique, BAK™ Lumbar Interbody Fusion System*, Brochure, 26 pgs., 1998.

SulzerMedica Sulzer Spine-Tech, *Spine Care Sulzer Spine-Tech Surgical Technique for Posterior Lumbar Fixation, Silhouette*, Brochure, 23 pgs., 1999.

SulzerMedica Sulzer Spine-Tech, *Spine Care Sulzer Spine-Tech, POLAr™ Instrumentation Surgical Technique*, Declaration of Daniel G. Schmiel and Brochure, 9 pgs., 2000.

Brantigan et al., State of the Art Reviews, *Posterior Lumbar Interbody Fusion Technique Using the Variable Screw Placement Spinal Fixation System*, vol. 6, No. 1, pp. 175-200, Jan. 1992.

Cheng, B. at al., North American Spine Society Proceedings, 14th Annual Meeting, *Biomechanical Evaluation of Transforaminal Oblique Cage Stability*, 3 pgs., Oct. 1999.

Harmes, J. et al., Thieme, *Instrumented Spinal Surgery, Principles and Techniques*, pp. 136-139, date unknown.

Patel, A. et al., Operative Techniques in Orthopaedics, *Posterior Lumbar Interbody Fusion with Metal Cages: Current Techniques*, vol. 10, No. 4, pp. 311-319, Oct. 2000.

Puno, R. et al., *The Puno-Winter-Byrd (PWB) Spinal System for Transpedicular Fixation of the Lumber Spine*, pp. 281-296, Mar. 18, 1997.

* cited by examiner

POSTERIOR OBLIQUE LUMBAR ARTHRODESIS

CROSS-REFERENCE TO RELATED APPLICATIONS

This application is a divisional of U.S. application Ser. No. 09/921,008, filed Aug. 2, 2001, which is a continuation-in-part of U.S. application Ser. No. 09/630,793, filed Aug. 2, 2000, now U.S. Pat. No. 6,626,905, which applications are incorporated herein by reference.

FIELD OF THE INVENTION

The invention pertains to interbody vertebral stabilization. Specifically, the invention is directed to devices and procedures for stabilization of vertebral bodies using external and intervertebral stabilizing systems. The invention is particularly advantageous for stabilizing lumbar vertebrae.

BACKGROUND OF THE INVENTION

Chronic back problems cause pain and disability for a large segment of the population. In many cases, the chronic back problems are caused by intervertebral disc disease and loss of stability of the intervertebral joint. Stabilization and/or arthrodesis of the intervertebral joint can reduce the pain and debilitating affects associated with disc disease.

Spinal stabilization systems and procedures have been developed to stabilize diseased intervertebral joints and, in some cases, to fuse the vertebrae that are adjacent to the diseased joint space. Most fusion techniques include removing some or all of the diseased disc material from the affected joint, stabilizing the joint and inserting a bone graft or other material to facilitate bony fusion of the vertebrae.

One type of spinal stabilization system includes screws and connecting rods which can be used for stabilizing many spinal conditions including, for example, degenerative disc disease, scoliosis, spondylolithisis and spinal stenosis. Examples of such systems are disclosed in U.S. Pat. Nos. 6,010,503; 5,946,760; 5,863,293; 4,653,481, etc., the entire disclosures of which are incorporated herein by reference. In these systems, a bone screw (e.g., pedicle screw) is typically anchored into each vertebral body to be stabilized and a rigid connecting rod mounted to the screws to fix the vertebrae in a particular relative position. Generally, these systems provide posterior column support but lack anterior column support.

Another type of spinal stabilization system includes interbody implants such as disclosed in, for example, U.S. Pat. Nos. 5,458,638; 5,489,307; 5,055,104; 5,026,373; 5,015,247; 4,961,740; 4,877,020; 4,743,256; and 4,501,269, the entire disclosures of which are incorporated herein by reference. Some of these implants are bone, some are solid titanium or similar non-bone implant material and some are hollow implants that provide for inclusion of a bone graft or other suitable material to facilitate bony union of the vertebrae.

Interbody implants can be inserted into the disc space through an anterior, posterior or lateral approach. When two implants are used, the implants are typically positioned parallel to one another on either side of a sagittal plane passing through the midline of the vertebral bodies. In some systems, the implants are inserted into a bore formed between adjacent vertebral bodies in the cortical endplates and can extend into the cancellous bone deep to the cortical endplates. Implant size is typically selected such that the implants force the vertebrae apart to cause tensing of the vertebral annulus and other soft tissue structures surrounding the joint space. Tensing the soft tissues surrounding the joint space results in the vertebrae exerting compressive forces on the implant to maintain the implant in place.

However, in some cases, the compressive forces exerted on the implant may cause undesired pressure induced changes to the bone adjacent the implant. Pressure induced changes can lead to reduced joint stability, increased fusion time and increased chance of subsidence or implant migration.

Accordingly, there is a continuing need for improved vertebral stabilizing devices and methods. The present invention is directed to addressing these needs.

SUMMARY OF THE INVENTION

The present invention is directed to instruments and methods for stabilization of vertebral bodies adjacent an intervertebral disc space using external stabilization systems and intervertebral implants.

In one embodiment, the invention provides a method for stabilizing an intervertebral joint between adjacent first and second vertebral bodies from a posterior approach. The method includes a step of forming an implant bore between the adjacent vertebrae for receiving an intervertebral implant. An intervertebral implant is then inserted into the implant bore. An external stabilization arrangement, such as known unilateral or bilateral pedicle screw and rod fixation systems can be mounted to the adjacent vertebrae before or after preparing the implant bore and inserting the intervertebral implant.

In another embodiment, the invention provides a surgical procedure for stabilizing an intervertebral joint between adjacent first and second vertebral bodies using an interbody implant inserted into the intervertebral disc space with the longitudinal axis of the implant oriented at an angle oblique to a sagittal plane passing through the midline of the vertebral bodies. Bilateral or unilateral external stabilization systems can be applied before or after insertion of the intervertebral implant.

The invention also provides new instruments including an instrument guide for guiding instruments for preparing an implant site and inserting the implant into the implant site. The instrument guide includes an internal lumen and a distal edge having an oblique angle that can rest on the exterior surface of the vertebrae such that the longitudinal axis of the guide can be at an angle oblique to a sagittal plane passing through the midline of the vertebral bodies. The instrument guides of the invention can also include one or more distally extending paddles to stabilize the instrument guide during use and to distract and/or maintain distraction of the intervertebral disc space to a predetermined height during an implant procedure.

Kits will also be available including instrument guides of the invention having various sized lumens and paddle widths for corresponding to different implant diameters and disc space heights. The kits can also include boring instruments, taps, depth gauges, distraction plugs, wedge distractors, etc., which may be necessary to perform a procedure according to the invention.

DETAILED DESCRIPTION OF THE INVENTION

The present invention is directed to stabilization of vertebral bodies adjacent an intervertebral joint space. The invention provides new instruments and procedures for cooperative interaction of external vertebral fixation systems, such as pedicle screws and rods, with interbody fusion systems to provide anterior and posterior column support which can result in greater fusion stability, greater motion segment stability, reduced fusion time, reduced pain, reduced chance of implant migration and reduced chance of subsidence.

It will be noted that in several places throughout the specification, guidance is provided through lists of examples. In each instance, the recited list serves only as a representative group. It is not meant, however, that the list is exclusive.

Screw and rod fixation systems suitable for the invention include known pedicle screw and rod fixation systems, non-limiting examples of which are disclosed in U.S. Pat. Nos. 6,010,503; 5,964,760; 5,863,293; the entire disclosures of which are incorporated herein by reference.

As used herein, an "implant" includes any interbody implant suitable for facilitating fusion between adjacent bones including intervertebral implants prepared from materials including non-bone implant materials such as titanium, stainless steel, porous titanium, ceramic, carbon fiber reinforced polymers, etc. or bone materials including heterologous, homologous, autologous, artificial bone, etc. The implants can be threaded or non-threaded. Non-limiting examples of implants suitable for the invention are disclosed in, for example, U.S. Pat. Nos. 5,865,847; 5,749,916; 5,722,977; 5,658,337; 5,609,636; 5,489,307; 5,484,638; 5,055,104; 5,026,373; 5,015,247; 4,961,740; 4,877,020; 4,848,757; 4,743,256; 4,501,269; and 3,848,601. The entire disclosure of each of these patents is incorporated herein by reference. A preferred embodiment of an implant is the BAK™ available from Sulzer Spine-Tech Inc., Minneapolis, Minn.

An "implant site" refers to the location for placement of the implant between adjacent vertebrae. An "implant bore" refers to the bore formed for receiving the implant between adjacent vertebrae. The implant bore can be threaded or non-threaded depending on the type of implant to be inserted and/or the stage of preparation of the implant bore. The implant bore can be prepared using drills, reamers, chisels or other instruments used for cutting bone or preparing a bore for receiving an implant.

If a hollow non-bone implant is used, after inserting the implant into an implant bore, the implant can be filled with a bone support matrix. As used herein, a "bone support matrix" is a material that facilitates new bone growth between the opposing vertebral bodies. Suitable bone support matrices can be resorbable or nonresorbable and osteoconductive or osteoinductive. Examples of suitable matrices according to the invention include synthetic materials, such as Healos™, available from Orquest, Mountain View, Calif.; NeOsteo™, available from Sulzer Orthopedic Biologics, Denver, Colo.; or any of a variety of bone morphogenic proteins (BMPs). Suitable bone support matrices also include heterologous, homologous, or autologous bone and derivatives thereof.

Throughout the specification, unless stated otherwise, the terms "proximal" and "distal" are relative terms, the term "proximal" referring to a location nearest the surgeon and the term "distal" referring to a location farthest from the surgeon. So, in the case of performing a vertebral fusion from an anterior approach, the anterior surfaces of the vertebrae are "proximal" and the posterior surfaces of the vertebrae are "distal" relative to the surgeon performing the procedure. Likewise, in a posterior approach, the posterior vertebral surfaces are proximal and the anterior surfaces are distal.

As used herein, the "depth" of a vertebrae is defined as the anterior posterior dimension of the vertebrae. The "width" of the vertebrae is the dimension from the right lateral edge to the left lateral edge. The "height" of the disc space is the dimension from the superior endplate to the inferior endplate of opposing vertebrae.

In one embodiment, the invention is directed to a surgical procedure for stabilizing vertebral bodies adjacent to an intervertebral disc space. According to this embodiment, a bilateral vertebral fixation system is used to provide posterior spinal column support and an intervertebral implant used to provide anterior spinal column support. An example of a preferred bilateral vertebral fixation system is a pedicle screw and rod fixation system. According to this embodiment, typically, at least one pedicle screw is inserted into the posterior aspect of the right and left lateral side of each vertebrae to be stabilized. The pedicle screws positioned on the left lateral side of each of the vertebrae to be stabilized are fixed together using a rod. Likewise, the pedicle screws positioned on the right lateral side of the vertebrae to be stabilized are fixed together using a rod. It will be appreciated that either the right or left lateral sides of the vertebrae can be fixed together first.

In another embodiment, a unilateral vertebral fixation system is used to provide posterior spinal column support. According to this embodiment, typically, a pedicle screw is inserted into the posterior aspect of either the right or left lateral side of each vertebrae to be stabilized. The pedicle screws are inserted on the same lateral side (i.e. right or left) of the vertebrae to be stabilized and are fixed together using a rod. It will be appreciated that either the right or left lateral sides of the vertebrae can be fixed together.

Before or after positioning the pedicle screws, and before or after fixation of the pedicle screws and rods, a single interbody spinal implant is inserted obliquely into each of the intervertebral disc spaces between adjacent vertebrae to be stabilized. According to the invention, "oblique" insertion of the implant means that the longitudinal axis of the implant is positioned in the intervertebral disc space at an angle of about 10-45°, typically about 20-25°, and preferably about 22.5° relative to a sagittal plane passing through the vertebral bodies. Because the implant is obliquely inserted, only a unilateral facetectomy or laminectomy is needed, thus preserving the existing facet joint of the contralateral side of the affected vertebrae.

In addition, while the pedicle screws can first be positioned and stabilized on either the right or left side, in one preferred embodiment, pedicle screw and rod stabilization can be performed first, and/or only, on the side of the vertebrae contralateral to the side from which the implant is inserted, prior to insertion of the implant. That is, if a right facetectomy and laminectomy is performed to insert the implant from the right side of the vertebrae, the left side of the vertebrae can be stabilized with the pedicle screw system prior to preparation of the implant site.

In some embodiments, it may be advantageous to distract the vertebral bodies prior to insertion of the spinal implant or pedicle screw fixation to change or restore the disc space to its normal height.

In another embodiment, the invention provides an instrument guide and kits including instrument guides, reamers, taps, distractors, etc. which are advantageous for performing the procedures of the invention.

DETAILED DESCRIPTION OF A PREFERRED EMBODIMENT

The invention will be described with reference to the accompanying drawings, wherein like reference numerals identify similar or corresponding components throughout the several views. The illustrated embodiments and description are for exemplary purposes to facilitate comprehension of the invention and should not be construed to limit the scope of the invention.

The invention can be used for stabilization of cervical, thoracic and lumbar vertebrae. For exemplary purposes, the invention will be described using a posterior approach to fuse the lumbosacral joint (i.e., $L_5$-$S_1$). It will be appreciated that in the lumbar region, insertion of an intervertebral implant according to the invention can be performed through an anterior approach and placement of the pedicle screw and rod through a posterior approach. However, combining an anterior and posterior approach requires repositioning of the patient during surgery, and thus, may not be preferred. In addition, although the following discussion exemplifies lumbar stabilization at a single level, multiple levels of vertebral stability can be performed using the herein described procedures.

For a posterior approach, the patient is placed in a prone position with the hips flexed and the legs adjusted to provide the desired sagittal alignment. Exposure of the disc space(s) to be fused can be made using known methods and decompression of the disc space can be performed as needed. An implant is selected that has the appropriate diameter and length for the patient. The diameter of the implant is preferably selected to provide sufficient distraction of the vertebrae to restore the normal disc height and to provide about 1 to 3 mm of purchase of the implant into the endplates of each of the superior and inferior vertebrae adjacent the affected disc space.

In one embodiment, a threaded implant having an external diameter of about 3-3.5 mm (i.e., outer thread diameter) greater than the distracted disc space height is selected to maximize disc space height while minimizing implant size. This embodiment provides about 1.5-1.75 mm of purchase of the threads into the endplates of each vertebra. In an alternative embodiment, if a non-threaded implant is selected an implant having an external diameter of about 0.75-1.25 mm greater than the distracted disc space can be selected. In some embodiments, the external diameter of the implant can be about equal to the disc space height. In such an embodiment, the implant maintains the disc space height without having purchase into the endplates of the vertebrae.

The length of the implant can be selected to maximize the amount of cortical bone at the exterior margin of the vertebral bodies that contacts the implant while still permitting the implant to reside completely within the exterior margins of the vertebral bodies. In other embodiments, a shorter implant may be selected to permit use of a greater amount of a bone support matrix in the disc space. An appropriate implant size can be determined using known methods including measurements based on pre-operative x-rays, CT images, MRI images or intra-operative x-rays. Templates can also be used such as, for example, BAK™, surgical measurement templates available from Sulzer Spine-Tech Inc., Minneapolis, Minn. Intra-operative fluoroscopy can also be used throughout the procedure.

Figure 1:
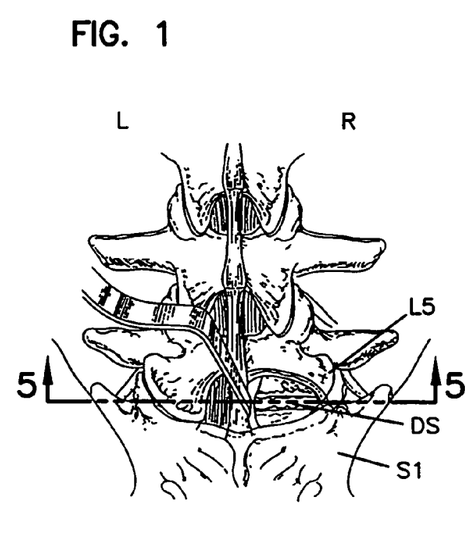
FIG. 1 is a posterior view of the $L_5$-$S_1$ vertebrae having a partial laminectomy and facetectomy on the right side.

FIG. 1 is a top view of the $L_5$-$S_1$ vertebrae and associated structures after partial unilateral laminectomy and facetectomy for exposure of the $L_5$-$S_1$ disc space DS for insertion of an implant from the right side of the disc space. While the implant can be inserted from either the right side or left side of the vertebrae, preferably the laminectomy and facetectomy are performed on the side with more symptomatic radiculopathic findings. Alternatively, the laminectomy and facetectomy can be performed in the side having less scar tissue if previous surgeries have been performed. In addition, while partial laminectomy may be performed on the side from which the implant will be inserted from, the entire lamina can be removed from the symptomatic side and some or all of the lamina can be removed on the contralateral side if believed to be necessary to obtain adequate disc and nerve root decompression. When using a hollow chambered implant, bone from the lamina and facet can be saved to pack into the chamber to facilitate new bone growth.

Figure 2:
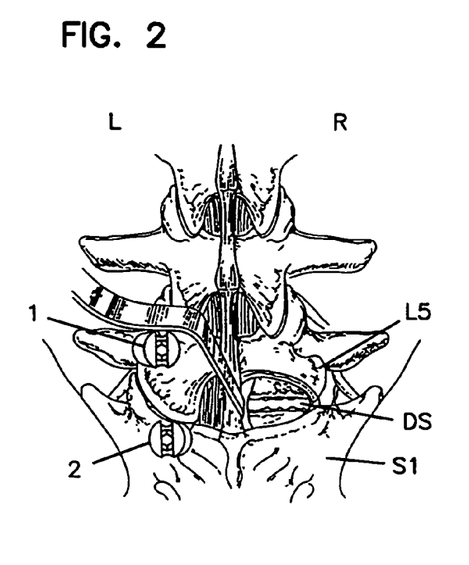
FIG. 2 is the same view of the $L_5$-$S_1$ vertebrae after discectomy.

Referring to FIG. 2, the exiting nerve root and thecal sac are retracted medially to provide exposure. Discectomy can then be performed as needed to remove disc material from the disc space DS. In the illustrated embodiment, a first pedicle screw 1 can be placed into left pedicle of the $L_5$ vertebrae and a second pedicle screw 2 can be placed into the left of the sacrum $S_1$. The pedicle screws are preferably positioned within the pedicle canal. In this embodiment, the pedicle screws are first placed on the side of the vertebrae contralateral to the side on which the laminectomy and facetectomy are performed. If the pedicle screws are placed prior to placement of the intervertebral implant, the vertebrae can be distracted and the rod secured between pedicle screws of the first side to maintain distraction of the vertebrae during preparation of the implant bore. Alternatively, as described below, distraction plugs can be used, alone or in combination with pedicle screws, if needed, to maintain distraction during preparation of the implant bore.

Figure 3:
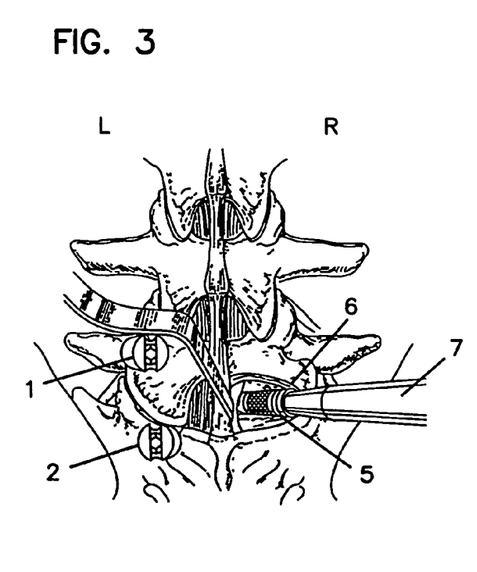
FIG. 3 is the same view of the $L_5$-$S_1$ vertebrae during insertion of a distraction plug into the disc space.
Figure 4:
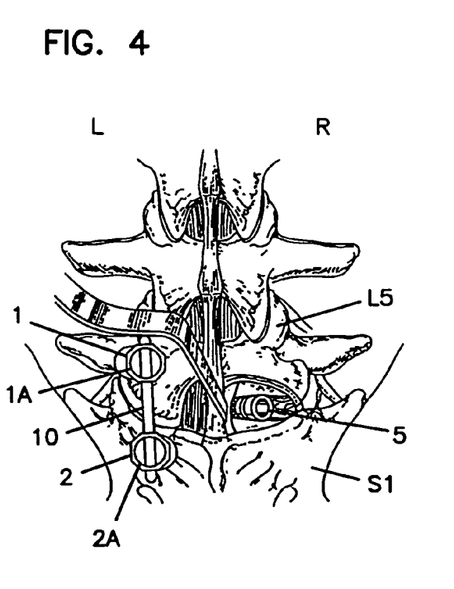
FIG. 4 is the same view of the $L_5$-$S_1$ vertebrae with the distraction plug in place.
Figure 12:
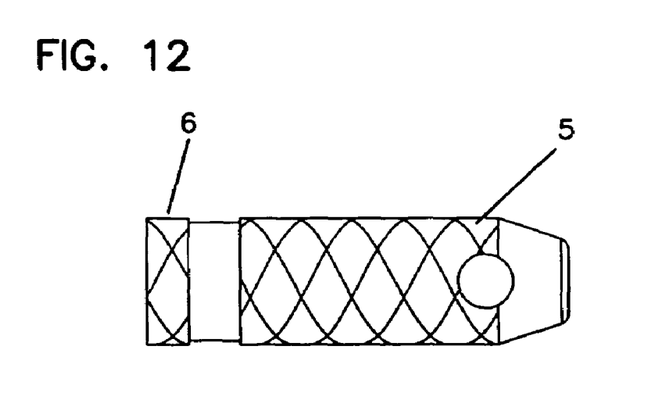
FIG. 12 is a side view of one embodiment of a distraction plug suitable for the invention.

Referring now to FIG. 3, the disc space DS can be sequentially distracted with distraction plugs 5 having incrementally increasing diameters to restore the disc space to a desired height. Distraction plugs suitable for the invention are known and disclosed in, for example, U.S. Pat. No. 5,489,307, the entire disclosure being incorporated herein by reference. A side view of an alternative embodiment of a distraction plug 5 suitable for the invention is shown in FIG. 12. As illustrated in FIG. 3, the proximal end 6 of distraction plug 5 can be mounted to a handle 7 for manipulating the distraction plug into the disc space DS. Also, as illustrated in FIG. 3, in preferred embodiments, the longitudinal axis of distraction plug 5 is inserted into disc space DS at an angle that is oblique to a sagittal plane passing through the midline of the vertebrae (i.e., mid-sagittal plane). As shown in FIG. 4, once appropriate distraction is achieved, a rod 10 can be applied between first pedicle screws 1 and 2 and the rod 10 secured using, for example, lock nuts 1a and 2a. In this embodiment, securing rod 10 at this stage provides distraction that can be maintained throughout the procedure. After securing rod 10 in position, distraction plug 5 can be removed.

In a further alternative embodiment, distraction of the vertebrae during preparation of the implant bore may be maintained solely via the insertion of a distraction plug 5. In this embodiment, pedicle screws 1, 2, along with a rod 10 secured therebetween, may be placed on either the same or contralateral side on which the laminectomy and/or facetectomy are performed. Placement of the pedicle screws 1, 2, with or without a rod 10, may precede or follow distraction with a distraction plug 5 and preparation of the implant bore (i.e., up to and including insertion of the implant).

Figure 5:
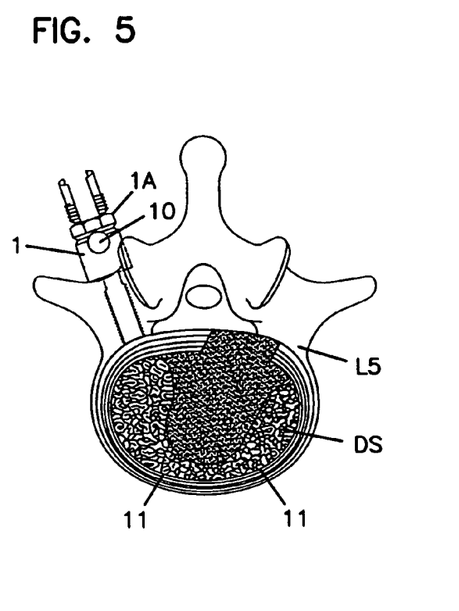
FIG. 5 is an end-on view of the $L_5$-$S_1$ disc space taken through line 5-5 of FIG. 1.
Figure 6:
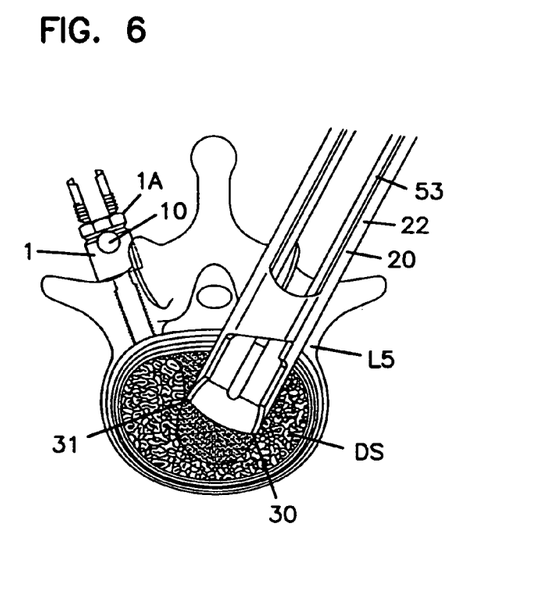
FIG. 6 is the same view of the $L_5$-$S_1$ disc space of FIG. 5 with an instrument guide and wedge distractor of the invention in place.

FIG. 5 is an end-on view of vertebral body $L_5$ taken through line 5-5 of FIG. 1. As illustrated, after removal of distraction plug 5, bone support matrix 11 can be packed into disc space DS lateral and anterior to the region where the implant site is to be formed. Referring to FIG. 6, an instrument guide 20 can then be used to guide instruments for preparation of the implant site. In the illustrated embodiment, a wedge distractor 53 is shown within the lumen of instrument guide 22 with paddles 30 and 31 passed into the disc space. Wedge distractor 53 fills the gap between paddles 30 and 31 and provides greater surface area contact with the vertebral endplates when the instrument guide is passed into the disc space.

In an alternative embodiment, the instrument guide 20 is used without the wedge distractor 53. In one form of this embodiment, the instrument guide 20 is placed over the distraction plug 5 and handle 7 and passed or impacted into the disc space. In another form of this embodiment (e.g., where sufficient distraction is provided by the pedicle screws and rod), the instrument guide 20 can be passed or impacted into the disc space alone.

Figure 13:
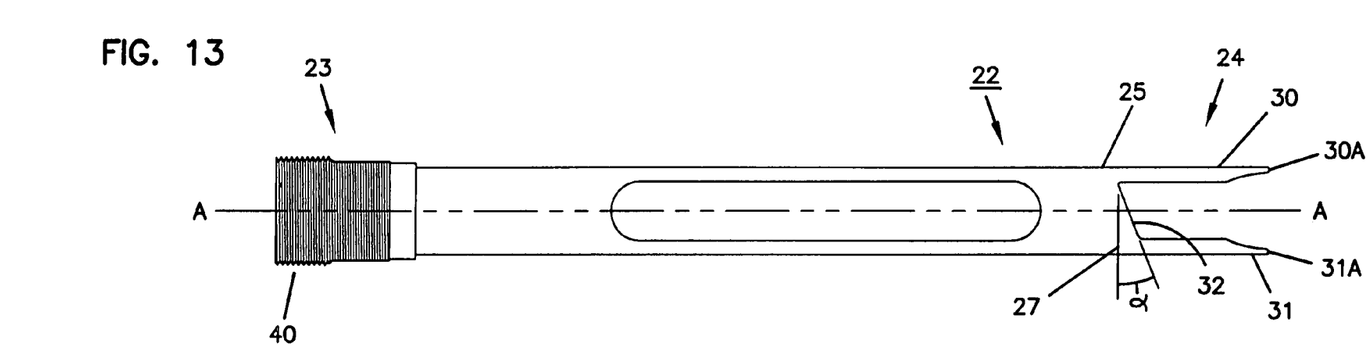
FIG. 13 is a side view of one embodiment of an instrument guide according to the invention.
Figure 14:
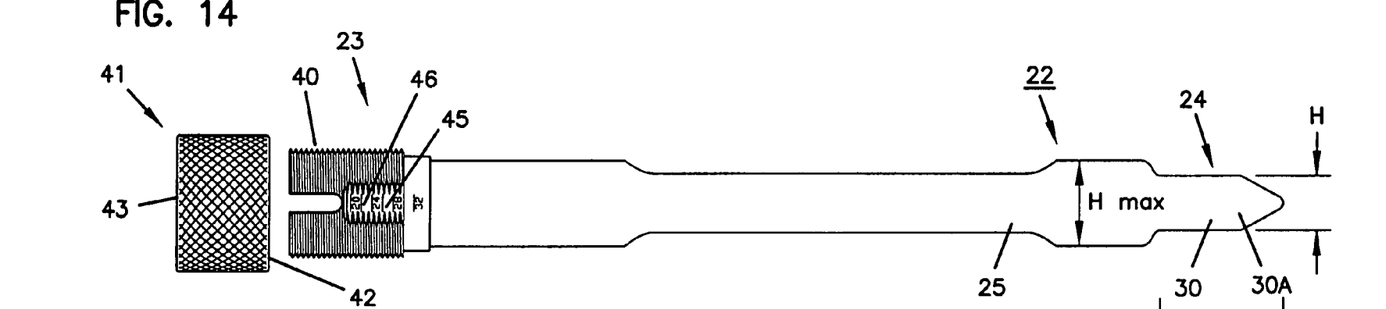
FIG. 14 is a side view of the instrument guide of FIG. 13 rotated 90° around the axis A-A.
Figure 15:
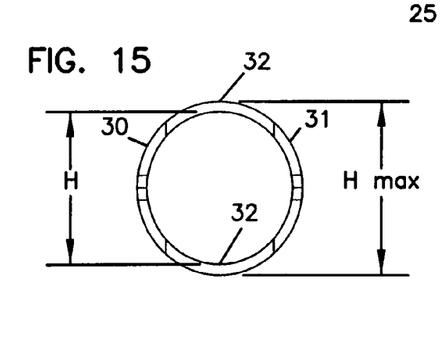
FIG. 15 is a distal end-on view of the instrument guide of FIG. 13.

FIGS. 13-15 illustrate one embodiment of a preferred instrument guide 22 according to the invention. FIG. 13 is a side view of instrument guide 22, FIG. 14 is a side view of instrument guide 22 rotated 90° from the view of FIG. 13 and FIG. 15 is a distal end view of instrument guide 22. Instrument guide 22 includes a proximal end 23, a distal end 24, a wall 25 surrounding a lumen 26 and having a longitudinal axis A-A passing therethrough. It will be appreciated that while instrument guide 22 has a circular cross-sectional configuration, an instrument guide of the invention can have other cross-sectional configurations including rectangular, oval, oblong, etc. The cross-sectional configuration of the instrument guide typically corresponds to the cross-sectional configuration of an implant to be inserted into an implant site prepared with the instrument guide.

Figure 18:
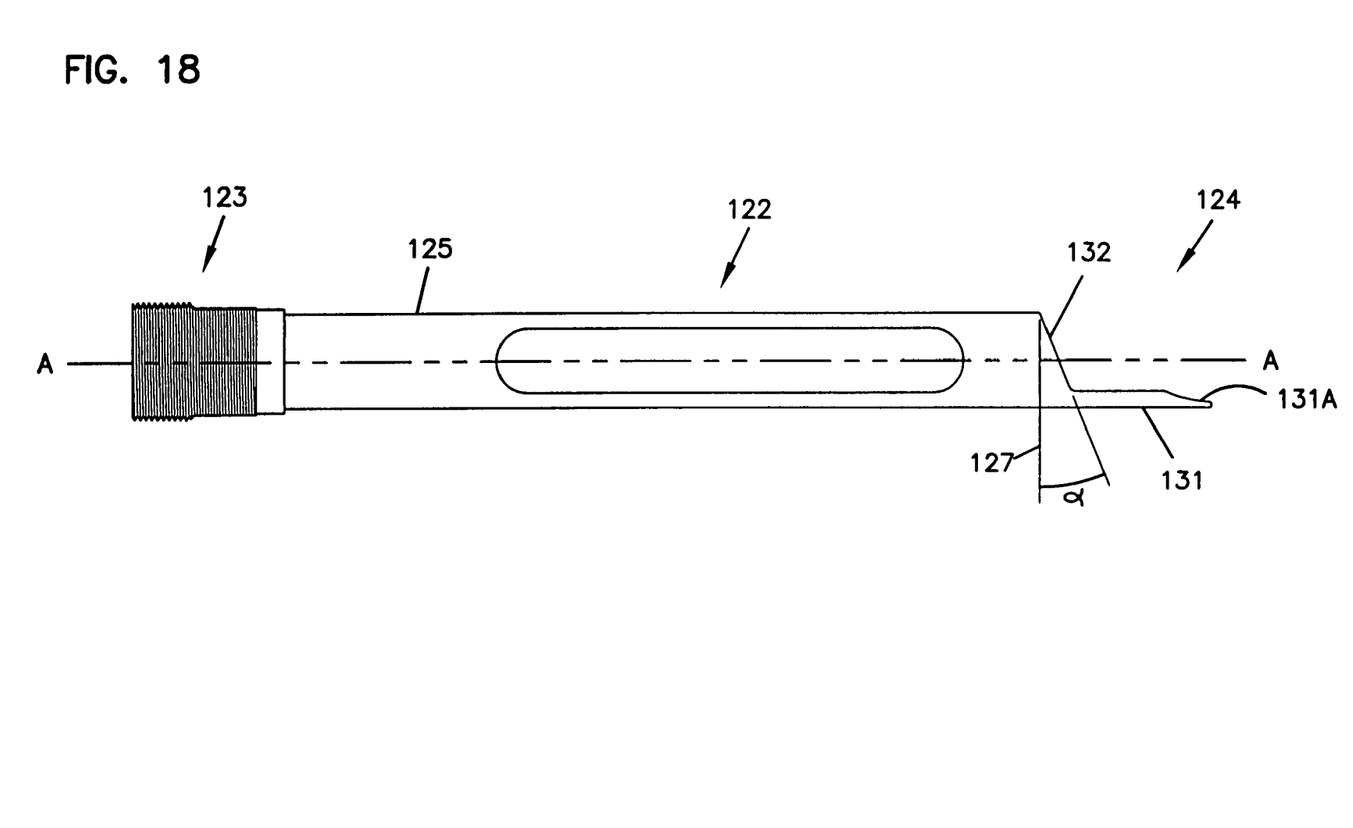
FIG. 18 is a side view of another embodiment of an instrument guide according to the invention.

The instrument guide 22 has one or more paddles extending from the distal end 24 (see e.g., FIGS. 13 and 18). In the illustrated embodiment, the instrument guide 22 has two paddles 30 and 31 extending from the distal end 24 of the instrument guide 22. As best appreciated in FIG. 13, the distal edge 32 of wall 25 of instrument guide 22 has an angle α, relative to longitudinal axis A-A, as distal edge 32 extends from paddle 30 to paddle 31. The angle α of distal edge 32 corresponds to the oblique angle at which the implant will be inserted into the disc space as further discussed below. In general, the angle of distal edge 32 can be about 10-30°, typically about 10-25° and, in one preferred embodiment, about 22.5° relative to longitudinal axis A-A. Thus, as will be appreciated from the drawings, when paddles 30 and 31 are inserted into disc space DS until distal edge 32 rests against the posterior surface of the vertebrae, longitudinal axis A-A will be oriented at an angle of α° from the mid-sagittal plane of the vertebrae. In this orientation, instrument guide 22 provides for orientation of all instruments passing through instrument guide 22 to be positioned at the same angle α relative to the mid-sagittal plane.

In an alternative embodiment shown in FIG. 18, instrument guide 122 includes a proximal end 123, a distal end 124, a wall 125 surrounding a lumen and having a longitudinal axis A-A passing therethrough. The instrument guide 122 has a single paddle 131 extending from the distal end 124. The distal edge 132 of wall 125 of instrument guide 122 has an angle α, relative to longitudinal axis A-A, as distal edge 132 extends from paddle 131 to wall 125. The angle α of distal edge 132 corresponds to the oblique angle at which the implant will be inserted into the disc space as further discussed below. In general, the angle of distal edge 132 can be about 10-30°, typically about 10-25° and, in one preferred embodiment, about 22.5° relative to longitudinal axis A-A. Thus, as will be appreciated from the drawings, when paddle 131 is inserted into disc space DS until distal edge 132 rests against the posterior surface of the vertebrae, longitudinal axis A-A will be oriented at an angle of α° from the mid-sagittal plane of the vertebrae. In this orientation, instrument guide 122 provides for orientation of all instruments passing through instrument guide 122 to be positioned at the same angle α relative to the mid-sagittal plane.

Embodiments with a single paddle 131 provide greater visibility of the implant site when the instrument guide 122 is placed with the paddle 131 distal to the surgeon. The single paddle instrument guide 122 also presents a lower profile and allows for a wider range of motion for instruments at the implant site.

Figure 19:
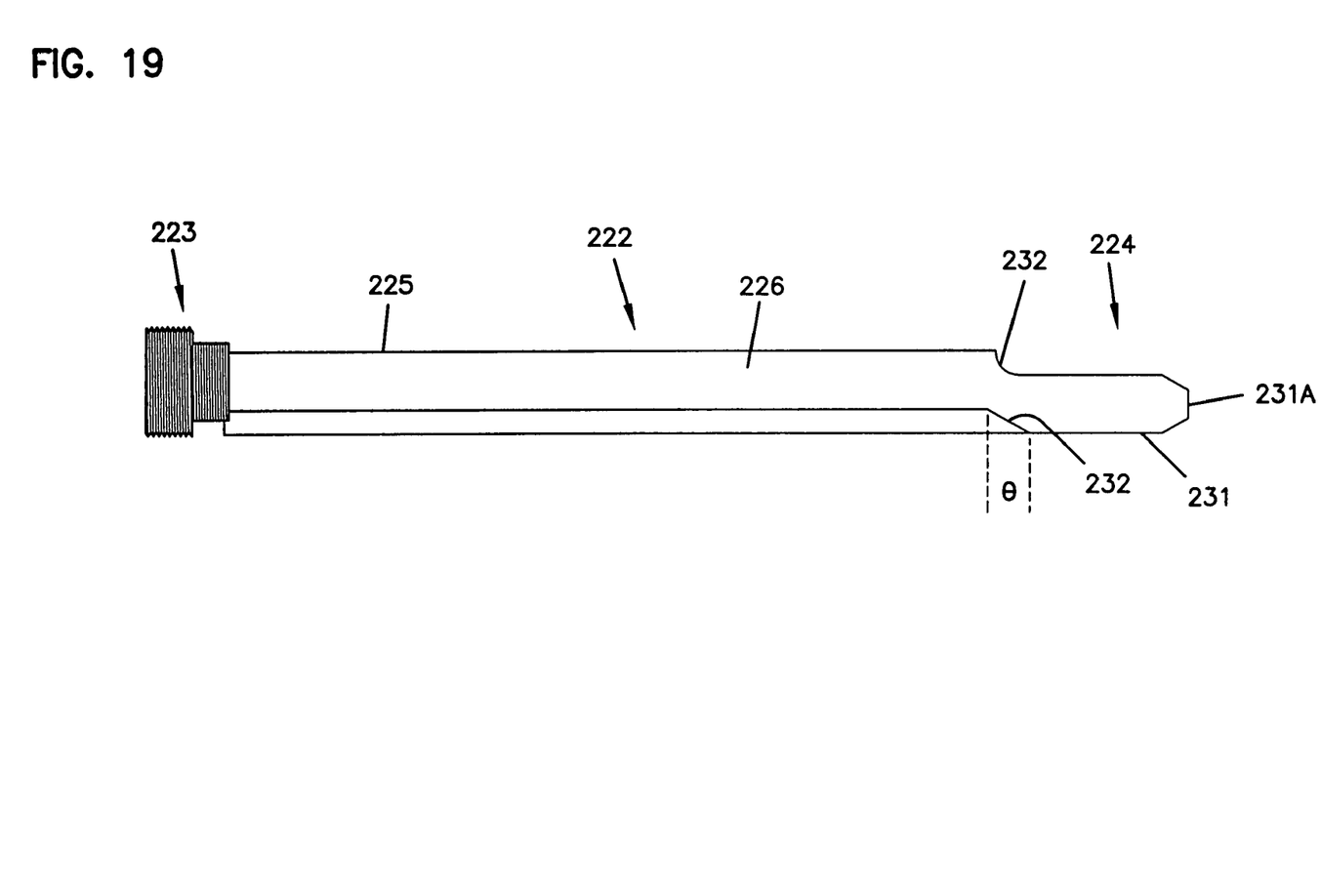
FIG. 19 is a side view of another embodiment of an instrument guide according to the invention.

Another embodiment of instrument guide 222 is shown in FIG. 19. In this embodiment, the instrument guide 222 includes a proximal end 223, a distal end 224, and a wall 225 at least partially surrounding a lumen 226. In a further embodiment, the wall 225 can completely surround the lumen 226. The instrument guide 222 has a longitudinal axis passing through the lumen 226, and at least one paddle 231 extending from the distal edge 232 of the wall 225. The distal edge 232 has an angle θ relative to the longitudinal axis, as distal edge 232 extends from wall 225 to paddle 231. The angle θ corresponds to the oblique angle at which the implant will be inserted into the disc space. In general, the angle θ can be about 10° to about 45°, typically about 10° to about 25°, and in one preferred embodiment, about 22.5° relative to the longitudinal axis. In a further embodiment, the instrument guide 225 has two paddles that are diametrically opposed.

Paddles 30, 31, 131, and 231 can also have a distal tapered tip, 30a, 31a, 131a, and 231a respectively, to facilitate insertion of paddles 30, 31, 131, and 231 into disc space DS. In addition, paddles 30, 31, 131, and 231 have a width dimension W. A plurality of instrument guides 22, 122, and/or 222 will be available having width dimensions W in about 1 mm increments to correspond with the disc height established by distraction plugs 5. Ranges of paddle widths suitable for instrument guide 22, 122, 222 according to the invention are about 2 to 20 mm.

The paddle width dimension W can be equal to or less than the cross-sectional diameter of the lumen 26 of instrument guide 22. Thus, in one embodiment, an instrument guide having a paddle width dimension W equal to the diameter of the lumen permits passage through the lumen of an implant having a diameter substantially equal to the disc space height formed by the paddle width dimension W.

In an alternative embodiment, the paddle width dimension W can be about 1 mm less than the diameter of the body of the implant. This relationship, referred to as "rule of one" distraction, provides for a smaller implant diameter to maintain a greater disc space height. According to the "rule of one," the lumen diameter of an instrument guide will typically be about 3.5 mm greater than the paddle width dimension W. As an example, for an instrument guide having a paddle width W of 12 mm, the lumen size of the instrument guide according to the "rule of one" can be calculated as follows. Assuming that the threads of the implant radially extend approximately 1.25 mm beyond the diameter of the body of the implant, an implant having a body diameter of 13 mm, such as a BAK™ 13 mm implant, has an overall diameter across the threads of 15.5 mm (13 mm+1.25 mm+1.25 mm). Accordingly, the lumen diameter of the instrument guide will be sized to permit passage of an implant diameter of 15.5 mm. Thus, the difference between the 12 mm paddle width dimension W and the lumen diameter of the instrument guide is about 3.5 mm. The difference between the 12 mm paddle width dimension W and the 13 mm body diameter is about 1 mm.

The proximal end 23 of instrument guide 22 can include a depth adjustment arrangement 35 for controlling the depth of penetration into the disc space of an instrument passed through instrument guide 22. For example, in one embodiment, the depth adjustment arrangement can include threads 40 at the proximal end 23 of instrument guide 22 which mate with internal threads 42 of cap 41. Thus, by threading cap 41 onto threads 40, the proximal surface of cap 43 acts as an affirmative stop to stop distal travel of an instrument passed into the instrument guide 22 that has a proximal end arrangement configured to abut against proximal end 43 of cap 41. An indicator arrangement 45 such as marks 46 can be used to indicate the depth of penetration of an instrument through the distal end 24 of instrument guide 33.

Figure 16:
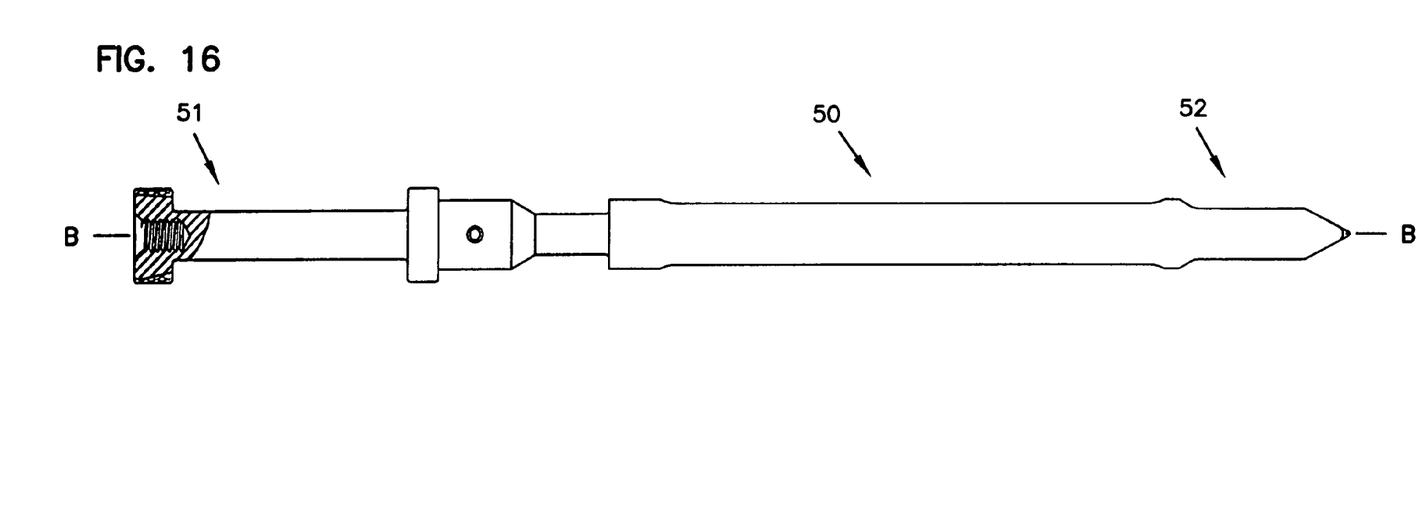
FIG. 16 is a side view of one embodiment of a wedge distractor according to the invention.
Figure 17:
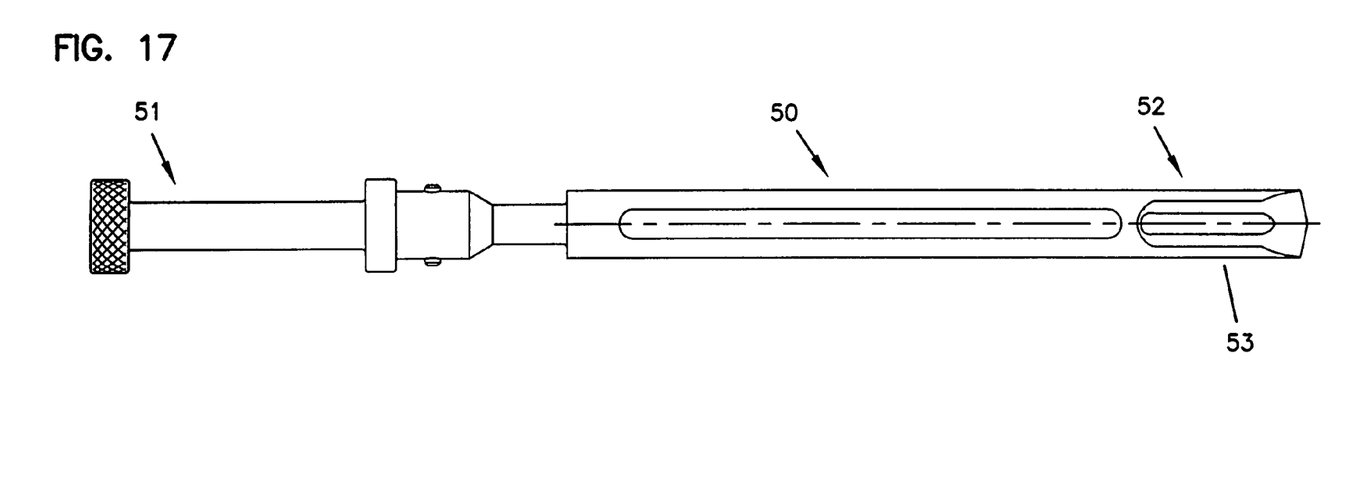
FIG. 17 is a top view of the wedge distractor of FIG. 16.

FIGS. 16 and 17 illustrate a wedge distractor 50 that can be passed into lumen 26 of instrument guide 22. As illustrated, wedge distractor 50 has a proximal end 51 and a distal end 52 and a longitudinal axis B-B passing therethrough. At distal end 52, wedge distractor 50 includes distal extension 53 configured to fit within the contours of paddles 30 and 31 of instrument guide 22.

Although the foregoing discussion of the method of the invention emphasizes distraction with a distraction plug prior to insertion of the paddles of instrument guide 22, in an alternative embodiment, the use of distraction plugs to distract the disc space may be omitted and distraction provided solely by insertion of the paddles of an instrument guide having a width dimension W equal to a desired disc space height.

Figure 7:
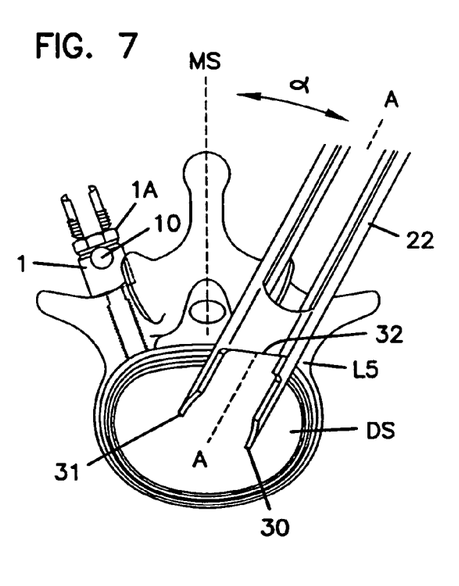
FIG. 7 is the same view of the $L_5$-$S_1$ disc space as FIG. 5 with an instrument guide of the invention in place.

Referring now to FIG. 7, it will be appreciated that when instrument guide 22 is distally advanced into disc space DS until distal edge 32 is substantially flush along the posterior margin of the vertebrae, angle α provides for the longitudinal axis A-A to be positioned at an angle α relative to mid-sagittal plane MS passing through the mid-line of the vertebrae.

Figure 8:
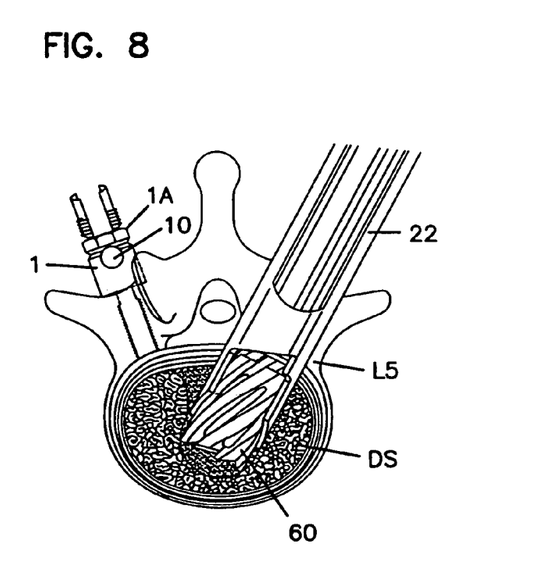
FIG. 8 is the same view of the $L_5$-$S_1$ disc space as FIG. 7 with a boring tool passed through the instrument guide.

Referring to FIG. 8, a reamer, drill, chisel or other boring instrument 60 can then be passed into instrument guide 22 and operated using known methods to form an implant bore between the end plates of the vertebrae. An implant bore formed in a preferred embodiment of the invention has a longitudinal axis that is at an angle oblique to the mid-sagittal plane.

Figure 9:
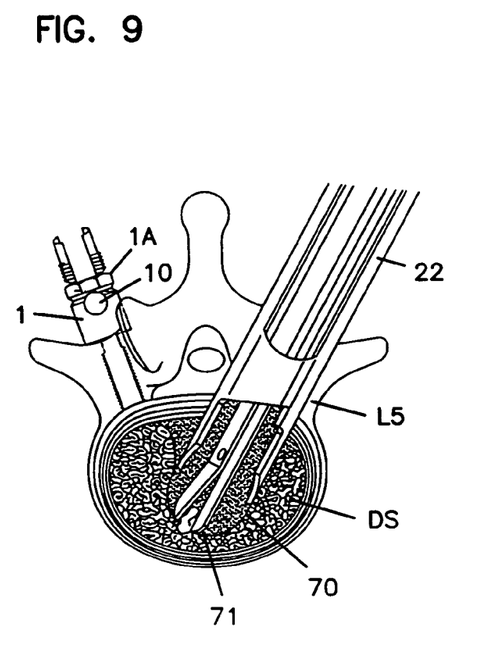
FIG. 9 is the same view of the $L_5$-$S_1$ disc space as FIG. 5 after boring an implant bore and showing a pituitary rongeur passed through the instrument guide for removing debris in the implant bore.

As shown in FIG. 9, debris remaining in the implant bore 70 prepared by boring tool 60 can be removed through instrument guide 22 using, for example, a pituitary rongeur 71. If a threaded implant is to be used, a tap can be passed through instrument guide 22 to tap threads into implant bore 70.

Figure 10:
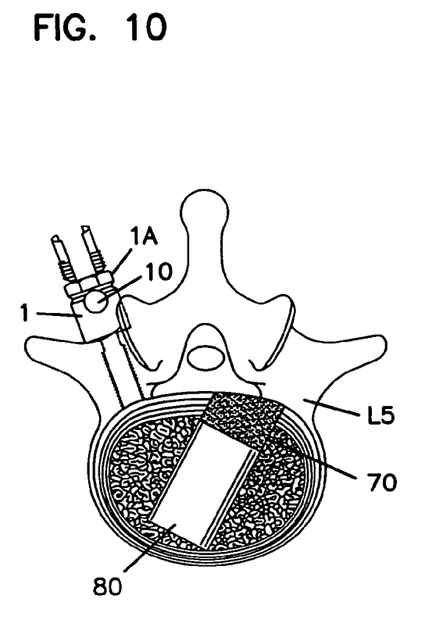
FIG. 10 is the same view of the $L_5$-$S_1$ disc space as FIG. 5 with an implant passed into the implant site.

As shown in FIG. 10, once the implant bore 70 is complete, an implant 80 can be passed into the bore. Implant 80 can be inserted into implant bore 70 through instrument guide 22, or instrument guide 22 can be removed and the implant inserted directly into the implant bore 70. The area posterior to the implant can then be packed with a bone support matrix such as autologous bone.

Figure 11:
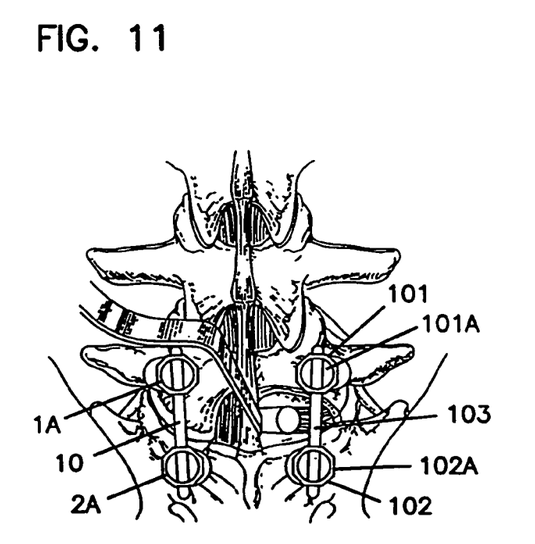
FIG. 11 is a posterior view of the $L_5$-$S_1$ vertebrae having a partial laminectomy and facetectomy on the right side after oblique insertion of an implant and bilateral pedicle screw and rod fixation.

Referring to FIG. 11, a second pedicle screw 101, 102 can then be inserted into the second side (right side) of vertebrae $L_5$ and $S_1$ and rod 103 applied between the pedicle screws and the rod secured in position, for example, by tightening lock nuts 101a and 102a.

If multiple levels are to be stabilized, the procedure described can be repeated at the additionally affected intervertebral disc space(s). While the preparation of the implant bore has been described using an instrument guide, such as instrument guide 22, it will be appreciated that the implant bore can also be prepared using other guide instruments or, if the surgeon prefers, free hand without angular guidance of the instruments by an instrument guide.

Oblique placement of a single implant into the intervertebral space provides at least two advantages. First, oblique placement of the implant reduces side to side rocking of the joint space that can occur when the implant is positioned within and parallel to the mid-sagittal plane of the disc space. In addition, by using only a single implant, only a single lamina and posterior facet joint need be removed to perform the procedure.

From the foregoing detailed description and examples, it will be evident that modifications and variations can be made in to the instruments and methods of the invention without departing from the spirit or scope of the invention. Therefore, it is intended that all modifications and variations not departing from the spirit of the invention come within the scope of the claims and their equivalents.

What is claimed is:

1. A kit for preparing an implant site for receiving an implant between adjacent first and second vertebrae, the kit comprising:

an instrument guide, said instrument guide comprising:
 (i) a tube having a longitudinal axis passing through a lumen of said tube, said lumen at least partially surrounded by a wall, said wall having a proximal end and a distal end;
 (ii) said distal end of said wall having a distal edge, said distal edge having an angle of about 10° to about 45° relative to a reference line perpendicular to said longitudinal axis and adapted to rest against, and in substantial contact with, a posterior surface of a human vertebra;
 (iii) at least one paddle extending from said distal edge of said wall; and (iv) an adjustable stop operatively connected to the tube to affirmatively stop instruments passed through said instrument guide;
wherein said adjustable stop includes a threaded portion threadedly engaged with a threaded portion of the tube of the instrument guide;
a distracting plug; and
an external vertebral stabilization device.

2. The kit according to claim 1 wherein said distal edge of said instrument guide has an angle of about 22° relative to a reference line perpendicular to said longitudinal axis.

3. The kit according to claim 1 further comprising a boring tool.

4. The kit according to claim 1 wherein the external vertebral stabilization device comprises two or more pedicle screws and at least one rod.

5. The kit according to claim 1 wherein the instrument guide includes visual markings to indicate the depth of penetration of an instrument through said instrument guide.

6. The kit according to claim 1 wherein the threaded portion of the adjustable stop includes external threads and the threaded portion of the tube includes internal threads.

7. The kit according to claim 6 wherein the instrument guide includes visual markings to indicate the depth of penetration of an instrument through said instrument guide.

8. A kit for preparing an implant site for receiving an implant between adjacent first and second vertebrae, the kit comprising:
an external vertebral stabilization device; and
an instrument guide, said instrument guide comprising:
(i) a tube having a longitudinal axis passing through a lumen of said tube, said lumen at least partially surrounded by a wall, said wall having a proximal end and a distal end;
(ii) said distal end of said wall having a distal edge, said distal edge having an angle of about 10° to about 45° relative to a reference line perpendicular to said longitudinal axis and adapted to rest against, and in substantial contact with, a posterior surface of a human vertebra;
(iii) at least one paddle extending from said distal edge of said wall; and
(iv) an adjustable stop operatively connected to the tube to affirmatively stop instruments passed through said instrument guide;
wherein said adjustable stop includes a threaded portion threadedly engaged with a threaded portion of the tube of the instrument guide.

9. The kit according to claim 8 wherein said distal edge of said instrument guide has an angle of about 22° relative to a reference line perpendicular to said longitudinal axis.

10. The kit according to claim 8 further comprising a boring tool.

11. The kit according to claim 8 wherein said external vertebral stabilization device comprises two or more pedicle screws and at least one rod.

12. The kit according to claim 8 wherein the instrument guide includes visual markings to indicate the depth of penetration of an instrument through said instrument guide.

13. The kit according to claim 8 wherein the threaded portion of the adjustable stop includes external threads and the threaded portion of the tube includes internal threads.

14. The kit according to claim 13 wherein the instrument guide includes visual markings to indicate the depth of penetration of an instrument through said instrument guide.

* * * * *

UNITED STATES PATENT AND TRADEMARK OFFICE
CERTIFICATE OF CORRECTION

PATENT NO. : 7,597,695 B2  Page 1 of 1
APPLICATION NO. : 11/364413
DATED : October 6, 2009
INVENTOR(S) : Schmiel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 545 days.

Signed and Sealed this

Fourteenth Day of December, 2010

David J. Kappos
*Director of the United States Patent and Trademark Office*